US010905516B2

(12) United States Patent
Senelier et al.

(10) Patent No.: US 10,905,516 B2
(45) Date of Patent: Feb. 2, 2021

(54) MEDICAL ILLUMINATION DEVICE WITH LEDS ORIENTED BY TABS PRE-CUT IN A PRINTED CIRCUIT BOARD

(71) Applicant: MAQUET SAS, Ardon (FR)

(72) Inventors: Gregory Senelier, Ardon (FR);
Jean-Philippe Breton, Ardon (FR);
Lionel Comte, Ardon (FR)

(73) Assignee: MAQUET SAS, Ardon (FR)

( * ) Notice: Subject to any disclaimer, the term of this patent is extended or adjusted under 35 U.S.C. 154(b) by 157 days.

(21) Appl. No.: 16/285,208

(22) Filed: Feb. 26, 2019

(65) Prior Publication Data
US 2019/0183598 A1 Jun. 20, 2019

Related U.S. Application Data

(63) Continuation of application No. PCT/FR2017/051132, filed on May 11, 2017.

(30) Foreign Application Priority Data

Sep. 5, 2016 (FR) .................................. 16 58229

(51) Int. Cl.
*A61B 90/30* (2016.01)
*F21V 5/00* (2018.01)
(Continued)

(52) U.S. Cl.
CPC ............. *A61B 90/30* (2016.02); *A61B 90/35* (2016.02); *F21S 4/22* (2016.01); *F21V 5/007* (2013.01);
(Continued)

(58) Field of Classification Search
CPC .. A61B 90/30; A61B 90/35; F21W 2131/205; F21S 4/22; F21V 5/007;
(Continued)

(56) References Cited

U.S. PATENT DOCUMENTS 8,292,804 B2 * 10/2012 Marka .................... A61B 90/35
600/249
8,454,197 B2 * 6/2013 Hauschulte ............. F21V 21/30
362/249.03
(Continued)

FOREIGN PATENT DOCUMENTS

| CN | 101280907 A | 10/2008 |
|---|---|---|
| CN | 102588833 A | 7/2012 |

(Continued)

OTHER PUBLICATIONS

Japanese Office Action (with English translation) dated Jan. 14, 2020 for corresponding Japanese Patent Application No. 2019-511396, 6 pages.
(Continued)

*Primary Examiner* — Alan B Cariaso

(57) ABSTRACT

A medical lighting device for illuminating an operative field, which device includes light-emitting diode (LED) light sources that cooperate with collimator optical systems to light the operative field. LEDs are mounted on a flat printed circuit board so that their illumination axes (B) passing through the collimator optical systems (7) have different angular orientations. The printed circuit board (6) may be cut out to form tongues, each of which is flexible and has a free end carrying an LED. Each tongue can be deformed under stress in such a manner that its free end is oriented substantially perpendicularly to the illumination axis (B).

20 Claims, 3 Drawing Sheets

(51) Int. Cl.
    *A61B 90/35*     (2016.01)
    *F21S 4/22*     (2016.01)
    *F21V 19/00*     (2006.01)
    *F21Y 107/50*     (2016.01)
    *F21Y 107/70*     (2016.01)
    *F21V 7/00*     (2006.01)
    *F21Y 115/10*     (2016.01)
    *F21W 131/205*     (2006.01)

(52) U.S. Cl.
    CPC ........ *F21V 7/0083* (2013.01); *F21V 19/0035* (2013.01); *A61B 2090/309* (2016.02); *F21V 19/004* (2013.01); *F21V 19/0045* (2013.01); *F21W 2131/205* (2013.01); *F21Y 2107/50* (2016.08); *F21Y 2107/70* (2016.08); *F21Y 2115/10* (2016.08)

(58) Field of Classification Search
    CPC .. F21V 7/0083; F21V 19/0035; F21V 19/004; F21V 19/0045; F21Y 2107/50; F21Y 2107/70
    See application file for complete search history.

(56) References Cited

U.S. PATENT DOCUMENTS

| | | |
|---|---|---|
| 2008/0023823 A1 | 1/2008 | Pike |
| 2012/0182731 A1 | 7/2012 | Kretschmann et al. |
| 2016/0097518 A1* | 4/2016 | Kim ........................ F21V 21/14 348/211.99 |
| 2016/0223181 A1* | 8/2016 | Benson .................... F21K 9/00 |
| 2016/0334067 A1* | 11/2016 | Yi .......................... F21K 9/232 |

FOREIGN PATENT DOCUMENTS

| | | |
|---|---|---|
| CN | 202484740 U | 10/2012 |
| CN | 104024723 A | 9/2014 |
| EP | 2031295 A1 | 3/2009 |
| WO | 2010/146534 A1 | 12/2010 |

OTHER PUBLICATIONS

Chinese Office Action and Chinese Search Report (with English translations) dated Feb. 27, 2020 for corresponding Chinese Patent Application No. 201780054115.0, 19 pages.

PCT Written Opinion dated Aug. 30, 2018 which issued for related PCT application No. PCT/FR2017/051132, 6 pages.

International Prelminary Report on Patentability dated Jan. 30, 2019 which issued for related PCT application No. PCT/FR2017/051132, 7 pages.

International Search Report dated Jun. 22, 2017 which issued for related PCT application No. PCT/FR2017/051132, 2 pages.

\* cited by examiner

MEDICAL ILLUMINATION DEVICE WITH LEDS ORIENTED BY TABS PRE-CUT IN A PRINTED CIRCUIT BOARD

RELATED CASES

Benefit and priority is claimed to PCT application PCT/FR2017/051132, filed May 11, 2017. Benefit and priority is also claimed to French application 1658229, filed Sep. 5, 2016.

TECHNICAL FIELD

The disclosure relates generally to a medical lighting device for illuminating an operative field, which device comprises a plurality of light-emitting diode (LED) light sources that co-operate with collimator optical systems to cause light to converge on the operative field, the LEDs being mounted on a flat printed circuit board in such a manner that their illumination axes passing through the collimator optical systems have different angular orientations.

BACKGROUND

In US2012/0182731, a medical lighting device can comprise a plurality of LED light sources mounted on a printed circuit board, the sources being coupled to collimator optical systems, the resulting assembly being arranged to cause light beams coming from the light sources to converge with different angular orientations towards the operative field so as to form an illumination spot.

In that device, the printed circuit board is sandwiched between a carrier structure and a support on which the collimator optical systems are mounted.

While that lighting device is being mechanically assembled, the support exerts mechanical pressure on the printed circuit board so as to cause non-flexible zones of the printed circuit board that carry the LED light sources to be oriented relative to the support so as to cause the light beams emitted by the light sources to converge.

In that device, the mechanical pressure is exerted by screwing. Adjusting the orientations of the optical elements on the support and adjusting the positions of the light sources on the printed circuit board to obtain the various different angular orientations are operations that can laborious.

Thus there is a need to simplify the assembly of the elements making up a medical lighting device by optimizing the assembly time and the adjustment steps.

SUMMARY

An object of the disclosure is to provide medical lighting devices to mitigate the above-mentioned drawbacks. The disclosure also includes convenient methods of assembly of lighting devices.

For example, the disclosure provides a medical lighting device for illuminating an operative field, which device comprises a plurality of light-emitting diode (LED) light sources that co-operate with collimator optical systems to cause light to converge on the operative field, the LEDs being mounted on a flat printed circuit board or similar in such a manner that their illumination axes pass through collimator optical systems having different angular orientations. The printed circuit board can be cut to form tongues or other shapes, each of which is flexible about a respective bending axis, and each of which has a flexible free end carrying an LED. The collimator optical systems can be received in recesses in a rigid support structure, with the recesses extending relative to one another in different axial directions that correspond to respective different angular orientations of the illumination axes. Each flexible tongue carrying an LED associated with a collimator optical system can be received in a recess in the support structure extending in a certain axial direction that is coplanar with the illumination axis of the collimator optical system. The tongue can be deformed under bending stress about the bending axis in such a manner that its flexible free end is oriented substantially perpendicularly to the illumination axis, and in that each flexible tongue is held, in the stressed deformed position, against the rigid support structure by screwing, adhesive bonding, thermoplastic staking, and/or by a catch on the support structure that locks by clipping onto the edge of the tongue.

The medical lighting devices of the disclosure may also have any combination of the following features:
- each flexible tongue is held in the stressed deformed position by a catch on said support structure that locks by clipping onto the edge of the free end of the tongue;
- each flexible tongue may have a bending axis that is substantially perpendicular to a longitudinal axis of the tongue and that may be formed by scoring;
- the collimator optical systems may be held by clipping in the recesses of the support structure;
- each collimator optical system may be provided with at least one positioning stud that comes to be engaged in a corresponding positioning hole provided in the free end of the corresponding tongue;
- the support structure can be made of molded plastic;
- it may be in the shape of a dome;
- the dome may be designed to be suspended from the ceiling of an operating theater, such as by a movable arm;
- the dome may be in the general shape of a cross formed by four lighting modules;
- the support structure may be secured to a carrier structure forming the frame of the dome;
- the flexible tongues may be obtained by cutting them out from the printed circuit board. The flexible tongue(s) may be planar sections of a planar PCB, which are bent or bendable so that their respective planes are at different angles from the other portions of the PCB;
- an LED may be placed at the free end of each tongue, said free end being for example disk-shaped; and
- each recess may be frustoconical in shape with the small base of that shape facing towards the carrier structure of the lighting and its large base facing towards the operative field.

The disclosure also provides methods of assembling lighting devices as described above, said methods being characterized by some or all of the following steps:
- inserting the collimator optical systems into the recesses in the support structure that are then locked in position by catches;
- then fastening the printed circuit board carrying the LEDs to the support structure in a certain relative position; and
- then bending the tongues towards the support structure until they come into abutment against the collimator optical systems and simultaneously locking them in position by means of the catches, or by other means.

During the method, a central screw may be used for fastening the printed circuit board carrying the LEDs to the support structure.

With this arrangement, it is possible to have one or more lenses and one or more LEDs distributed over one or more printed circuit boards.

Fastening the elements together by clipping simplifies the fastening, but it is also possible to use fastening by screwing, adhesive bonding, staking or the like.

Fastening by clipping offers the advantage of making it possible to more easily disassemble the elements.

The most preferred arrangement offers the advantage of being simple to implement because the interface support for the collimator optical systems performs various different functions. For example, a mechanical function of carrying the optical systems, and an optical adjustment function for orienting the illumination axes of the LEDs.

For cutting out the flexible tongues from the printed circuit board, it can be useful to provide each tongue with a bending axis that is substantially perpendicular to the longitudinal axis of the tongue. The bending axis may be designed in different manners within the knowledge of the person skilled in the art, e.g. by scoring a line. This may use, for example, a flat rectangular PCB (which includes square PCBs) which has one, two, or more tongues cut from the rectangular PBC so that they can bend away from the plane of the original rectangular PCB.

Lighting devices according to the disclosure may include some or all of the following:

Light-emitting diodes (LEDs) mounted on a flat printed circuit board (PCB), the PCB comprising a plurality of tongues, the tongues being flexible about respective bending axes (P), each tongue having a free end and carrying a respective LED of said plurality of LEDs.

It may include a support structure, the support structure being rigid, and comprising a plurality of recesses, wherein at least some of said plurality of recesses extend in different axial directions relative to other of said plurality of recesses, and wherein said different axial directions correspond to different angular orientations of illumination axes (B).

It may include collimators, the collimators being in respective recesses of the support structure, the collimators each being aligned with the axial directions of their corresponding recesses, the collimators each also being aligned with respective illumination axes (B).

In useful embodiments each tongue is associated with a respective collimator such that the respective LED is aligned with the collimator in the respective recess in the support structure, and aligned with the respective illumination axis (B). Each tongue can be oriented in a respective axial orientation (C), the axial orientation (C) being perpendicular with the respective illumination axis (B). Each tongue may be deformed relative to other areas of the PCB, for example about the respective bending axis (P), to be oriented in the respective axial orientation (C). In the bent/deformed orientation, each tongue is held in its respective deformed position against the support structure, for example by at least one of: screwing, adhesive bonding, thermoplastic staking, and a respective catch on the support structure which locks the tongue in place by clipping onto an edge of the tongue. The tongues may snap into clipping/catch structures as part of the process of bending the tongues forward into position, for added convenience.

BRIEF DESCRIPTION OF THE DRAWINGS

The disclosure can be better understood with reference to the drawings showing exemplary embodiments.

DESCRIPTION OF EXEMPLARY EMBODIMENTS

Figure 1:
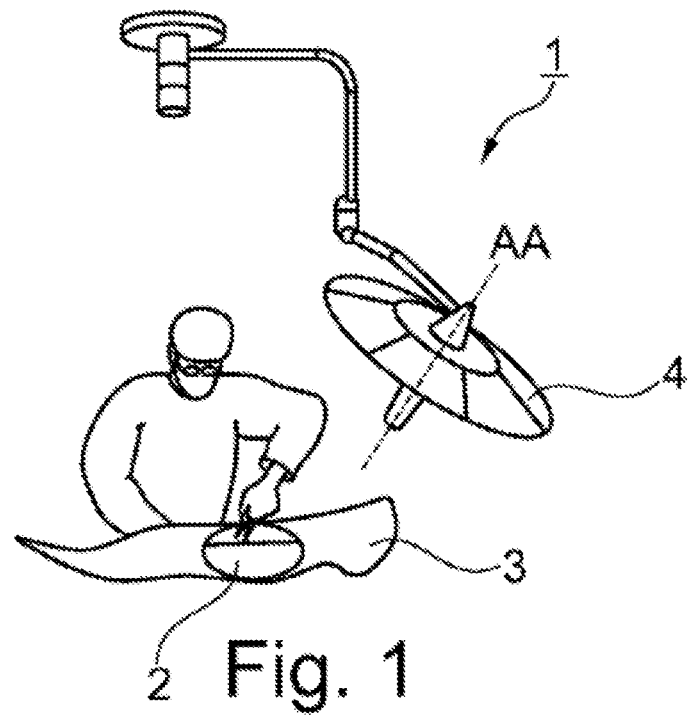
FIG. 1 is a diagrammatic view of a medical lighting device having an axial lighting dome for illuminating an operative field.

FIG. 1 shows a medical lighting device 1 used in an operating theater for forming an illumination spot 2 on an operative field 3.

The lighting device 1 in this example is in the shape of a dome 4 that is suspended from the ceiling of the operating theater and that generally has an illumination axis indicated by reference AA.

Figure 2:
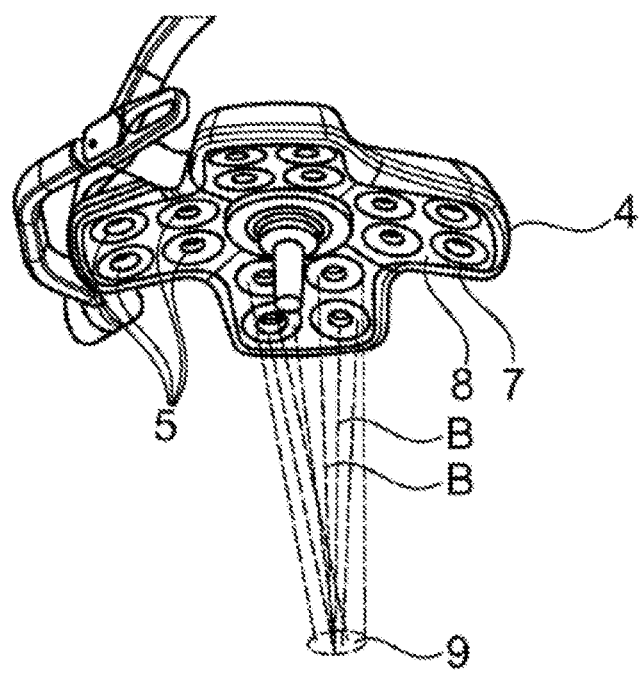
FIG. 2 is a perspective view of the front face of a lighting device.

FIG. 2 is a perspective view showing the front face of a lighting device 1 that is analogous to the FIG. 1 lighting device, the dome 4 in this example being in the general shape of a cross formed by four lighting modules, each having four light sources 5, which, in this example are LEDs distributed at respective ones of the four corners of a square.

Figure 3:
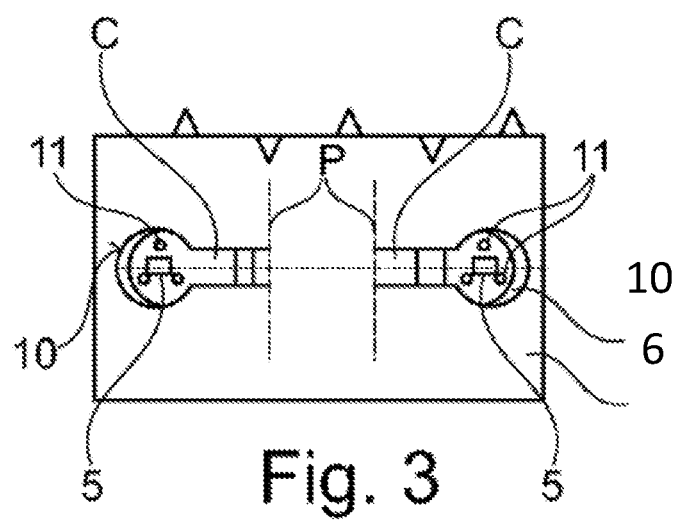
FIG. 3 is a diagrammatic plan view of a portion of a printed circuit board that is cut out in accordance with the disclosure.

The LEDs are mounted on a printed circuit board 6 that is flat before it is installed in the lighting device 1, as shown in FIG. 3.

In FIG. 2, the dashed lines indicate the respective illumination axes B of four LEDs of a lighting module so as to show that they converge on the operative field 3 so as to form an illumination spot 2 of greater or smaller size.

Said illumination axes B thus have angular orientations that are different, but are preferably oriented so that they converge.

In FIG. 2, reference 7 designates a collimator optical system 7 or lens that is mounted in an interface support structure 8 in which a plurality of collimator optical systems 7 are placed.

Figure 5:
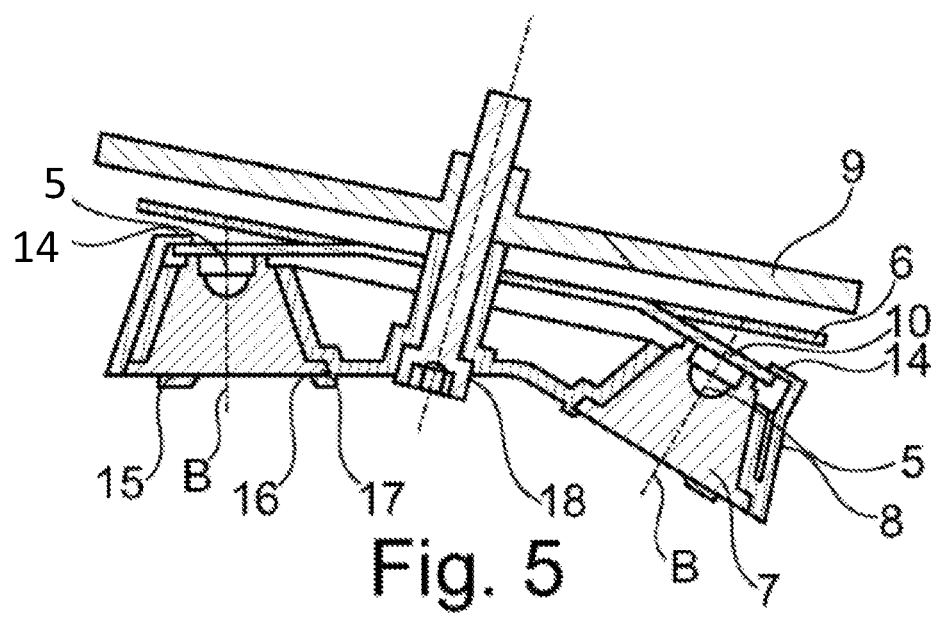
FIG. 5 is a cross-section view of a portion of a medical lighting device according to the disclosure.

The support structure 8 is secured to a carrier structure 9 forming the frame of the lighting dome 4 as shown in FIG. 5.

In this example, FIG. 3 shows a portion of a printed circuit board (PCB) 6 that is rigid and flat before it is installed in the dome 4. The printed circuit board 6 may be formed with flexible tongues 10, each of which extends in a certain axial direction indicated by reference C so that it can be deformed by bending. Flexible "tongue" sections of the PCB carrying LEDs may have various shapes, in addition to the example depicted. The PCB 6 may be a unitary planar board, with one or more planar "tongues" 10 cut out such that they can bend forward away from a plane of the PCB 6 to be facing in a different orientation.

The flexible tongues 10 may be obtained by cutting them out from the printed circuit board 6. For example, the tongues may be elongated sections cut from a flat rectangular PCB, which can bend out of the plane of the original rectangular PCB.

In FIG. 3, reference P indicates the bending axis for each tongue 10.

FIG. 3 shows an LED placed at the free end of each tongue 10, which free end is disk-shaped in this example.

The length of each tongue 10 may be a few centimeters.

In this example, each flexible tongue 10 is provided at its free end with three positioning cutouts or holes 11 placed in a triangle configuration around the LED. These positioning holes 11 are designed to receive corresponding positioning studs 12 that are provided on each collimator optical system 7 for engagement and alignment therewith.

Figure 4A:
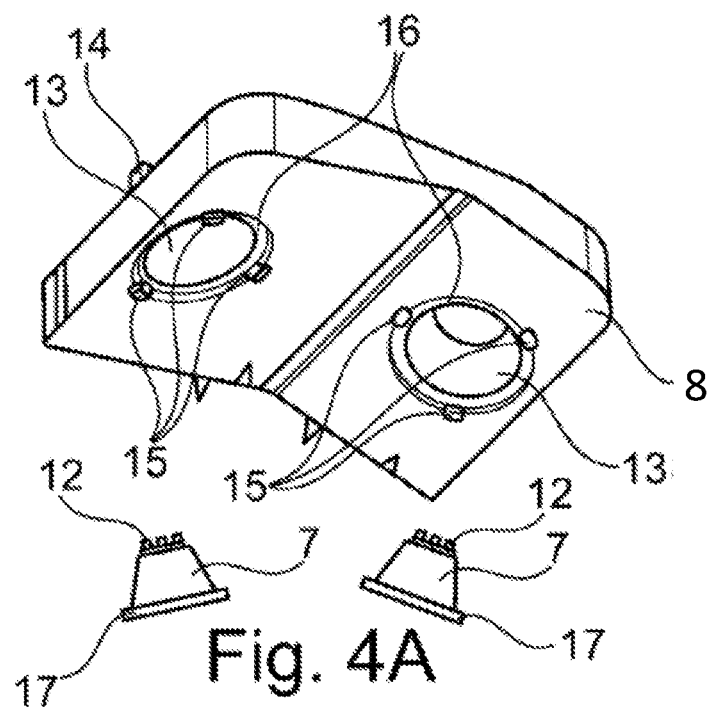
FIG. 4A is a perspective view from below showing a support structure for collimator optical systems of the lighting device of the disclosure.
Figure 4B:
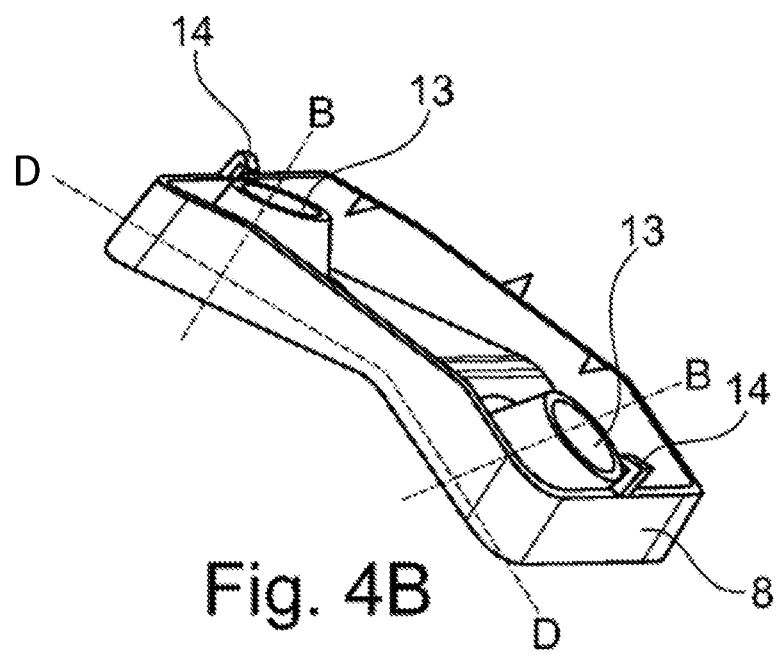
FIG. 4B is a perspective view from above of the support structure shown in FIG. 4A.

In this embodiment, the collimator optical systems 7 are received in recesses 13 in the support structure 8 that are shown in FIGS. 4A and 4B.

In these FIGS. 4A and 4B, the support structure 8 is shown in fragmentary manner, with only two recesses 13. Thus, the support structure may be larger and include more than two recesses, such as shown in FIG. 2.

Said interface support structure 8 is advantageously made of a molded plastics material.

The recesses 13 can extend in the molded support structure 8 relative to one another in different axial directions such as those indicated by reference B in FIG. 4B, and that correspond to respective ones of the angular orientations of the illumination axes B in FIG. 2. Each flexible tongue 10 carrying an LED can be associated with a respective collimator optical system 7 received in a recess 13 in the interface support structure 8. The tongues can extend in a longitudinal direction indicated by reference C in FIG. 3 that is perpendicular with the respective illumination axis B. The tongues can be deformed under bending stress about the bending axis P so that their free end comes to be placed substantially perpendicularly to the corresponding illumination axis B of the collimator optical system 7.

In the example shown in FIGS. 4A and 4B, each recess 13 is frustoconical in shape with the small base of that shape facing towards the carrier structure 9 of the lighting and its larger base facing towards the operative field 3.

One face of the support structure 8 may be provided with flexible catches 14 that can be seen in FIG. 4B at the periphery of the small base of each of the recesses 13, which catches serves to hold the tongues 10 in the stressed deformed position (bent position) as can be seen in FIG. 5.

Said catch 14 is locked, e.g. by clipping, in this example onto the edge of the tongue 10 and more precisely onto the circular edge of the free end of the tongue 10.

On the other face of the interface support structure 8, in this example three flexible catches 15 that can be seen in FIG. 4A are provided at the periphery of the large base of each of the recesses 13, which catches serve to hold the collimator optical systems 7 in position in the recesses 13, e.g. by clipping.

Reference 16 in FIG. 4A designates an annular shoulder 16 serving as a holding abutment for holding the collimator optical systems 7 in the recesses 13.

The collimator optical systems 7 that are shown diagrammatically in FIG. 4A are of shape complementary to the shape of the recesses 13, with a large base provided with a circular rim 17 and a small base provided with positioning studs 12, which, in this example project axially relative to the axis of the cone while extending towards the outside of the cone.

In order to assemble the lighting device 1, firstly the collimator optical systems 7 may be inserted into the recesses 13 in the interface support structure 8 and said collimator optical systems are then locked in position by the catches 15.

Then the printed circuit board 6 carrying the LEDs 5 is fastened to the support structure 8 in a certain relative position, e.g. by means of a central screw 18 that is shown highly diagrammatically in FIG. 5.

Then the tongues 10 are folded towards the support structure 8 until they come into abutment against the collimator optical systems 7 and are simultaneously locked in position by the catches 14, as shown in FIG. 5.

Finally, the resulting assembly is secured to the carrier structure 9 of the lighting dome.

There is preferably no separate additional step of adjusting the positions of the collimator optical systems 7 because, as installed in the interface support structure 8, they are already automatically oriented in a convergent manner in and/or against the interface support structure 8.

In addition, it is preferably not necessary to deform the entire printed circuit board 6 in order to obtain different angular orientations for the LED light sources 5, aligned with the corresponding collimators.

Exemplary embodiments may include a medical lighting device 1 for illuminating an operative field 3, which device comprises a plurality of light-emitting diode (LED) light sources 5 that co-operate with collimator optical systems to cause light to converge on the operative field 3, said LEDs being mounted on a flat printed circuit board 6 in such a manner that their illumination axes (B) passing through the collimator optical systems have different angular orientations, said medical lighting device being characterized in that said printed circuit board 6 is cut out to form tongues 10, each of which is flexible about a respective bending axis (P), and each of which has a flexible free end carrying an LED, in that said collimator optical systems 7 are received in recesses 13 in a rigid support structure 8, said recesses 13 extending relative to one another in different axial directions that correspond to respective ones of said different angular orientations of said illumination axes (B), in that each flexible tongue 10 carrying an LED that is associated with a collimator optical system 7 received in a recess 13 in said support structure extends in a certain axial direction (C) that is coplanar with said illumination axis (B) of said collimator optical system 7 and is deformed under bending stress about said bending axis (P) in such a manner that its flexible free end is oriented substantially perpendicularly to said illumination axis, and in that each flexible tongue is held, in the stressed deformed position, against the rigid support structure 8 by screwing, adhesive bonding, thermoplastic staking, or by a catch 14 on said support structure 8 that locks by clipping onto the edge of said tongue 10.

In some embodiments each flexible tongue 10 is held in the stressed deformed position by a catch 14 on said support structure 8 that locks by clipping onto the edge of said free end of said tongue 10.

In some embodiments each flexible tongue 10 has a bending axis (P) that is substantially perpendicular to a longitudinal axis (C) of said tongue and that is formed by scoring. Collimator optical systems 7 may be held by clipping in recesses 13 of the support structure 8. Each collimator optical system 7 can be provided with at least one positioning stud 12 engaged in a corresponding positioning hole 11 provided in a free end of the corresponding tongue 10.

The overall lighting device may be in the shape of a dome 4, or another shape. The device may be suspended from an arm, such as for use in an operating theatre. The dome 4 can be in the general shape of a cross formed by four lighting modules.

Methods of assembling lighting devices disclosed herein can include some or all of the following steps:

inserting collimator optical systems 7 into recesses 13 in the support structure 8, and then locking them in position by catches 15;

then fastening said printed circuit board 6 carrying said LEDs 5 to the support structure 8 in a certain relative position; and then bending said tongues 10 towards said support structure 8 until they come into abutment against the collimator optical systems 7 and simultaneously locking them in position by means of said catches 14. Based on the shape of the back side of the support structure and the alignment of the collimators 7 by the recesses 7, the LEDs 5 on the tongues can be automatically aligned with respective collimators simply by bending the tongues forward against the back of the support structure and fixing the tongues in place. A screw 18 or other means can be used to fasten the printed circuit board PCB 6 to the support structure 8.

The devices and methods can also be achieved with lighting elements other than LEDs.

The embodiments disclosed above are useful examples of the disclosed devices and methods. Persons of skill will recognize that certain variations are possible in implementing this disclosure.

The invention claimed is:

1. A medical lighting device for illuminating an operative field, the medical lighting device comprising:
    a plurality of light-emitting diodes (LEDs) mounted on a flat printed circuit board (PCB);
    the PCB comprising a plurality of tongues, the tongues being flexible about respective bending axes (P), each tongue having a free end and carrying an LED of said plurality of LEDs;
    a support structure, the support structure being rigid, and comprising a plurality of recesses, wherein at least some of said plurality of recesses extend in different axial directions relative to other of said plurality of recesses, and wherein said different axial directions correspond to different angular orientations of illumination axes (B);
    collimators, the collimators being in respective recesses of the support structure, the collimators each being aligned with the axial directions of their corresponding recesses, the collimators each also being aligned with respective illumination axes (B);
    wherein each tongue is associated with a respective collimator such that the respective LED of the tongue is aligned with the collimator and also with the respective illumination axis (B);
    wherein each tongue is oriented in a respective axial orientation (C), the axial orientation (C) being perpendicular with the respective illumination axis (B);
    wherein each tongue is deformed relative to other areas of the PCB about the respective bending axis (P), to be oriented in the respective axial orientation (C);
    wherein each tongue is held in its respective deformed position against the support structure by at least one of: screwing, adhesive bonding, thermoplastic staking, and a respective catch on the support structure which locks the tongue in place by clipping onto an edge of the tongue.

2. The medical lighting device according to claim 1:
    wherein each tongue is held in its respective deformed position against the support structure by a respective catch on the support structure which locks the tongue in place by clipping onto an edge of the tongue.

3. The medical lighting device according to claim 1:
    wherein the bending axis (P) of each tongue is substantially perpendicular to the axial orientation (C) of the respective tongue.

4. The medical lighting device according to claim 1:
    wherein the collimators are held in their respective recesses by clipping into notches on the support structure.

5. The medical lighting device according to claim 1:
    wherein each collimator comprises at least one positioning stud, the at least one positioning stud being engaged in a corresponding at least one positioning hole in the free end of the respective tongue associated with the collimator.

6. The medical lighting device according to claim 1:
    wherein the support structure comprises molded plastic.

7. The medical lighting device according to claim 1:
    wherein the lighting device is in a shape of a dome; and
    wherein the lighting device is connected to a movable suspension arm, the suspension arm being configured for suspension in an operating theatre.

8. The medical lighting device according to claim 1:
    wherein the lighting device is in a shape of a cross formed by four lighting modules.

9. The medical lighting device according to claim 1:
    wherein the lighting device is in a shape of a dome;
    further comprising a carrier structure forming a frame of said dome;
    wherein the support structure is connected to the carrier structure.

10. The medical lighting device according to claim 1:
    wherein the tongues are each planar sections cut from the PCB.

11. The medical lighting device according to claim 1:
    wherein the tongues are each planar sections cut from the PCB, and are connected to the PCB at their respective bending axes (P).

12. The medical lighting device according to claim 1:
    wherein the LEDs are at the free end of their respective tongues.

13. The medical lighting device according to claim 1:
    wherein the recesses and collimators are frustoconical in shape, with the larger bases of the recesses and the collimators oriented towards an operating field.

14. A method of assembling the medical lighting device according to claim 1, the method comprising:
    inserting said collimators into said recesses in the support structure;
    fastening the PCB to a rear side of the support structure;
    after said fastening the PCB to the rear side of the support structure, bending said plurality of tongues of the PCB towards and against a rear side of the support structure, until the LEDs of the tongues are positioned adjacent respective collimators; and
    after said bending, locking the tongues against the support structure in a bent position by at least one of: screwing, adhesive bonding, thermoplastic staking, and clipping catches of the support structure onto the tongues.

15. A method of assembling the medical lighting device according to claim 1, the method comprising:
    fastening the PCB to a rear side of the support structure;
    bending said plurality of tongues of the PCB towards a rear side of the support structure, until the LEDs of the tongues are positioned adjacent respective collimators; and as part of said bending, locking the tongues against the support structure in a bent position by clipping catches of the support structure onto edges of the tongues.

16. A medical lighting device for illuminating an operative field, the medical lighting device comprising:
    a plurality of light-emitting diodes (LEDs) mounted on a printed circuit board (PCB);
    the PCB comprising a plurality of tongues, each tongue having a free end and carrying a respective LED of said plurality of LEDs;
    a support structure, the support structure comprising a plurality of recesses, wherein at least some of said plurality of recesses extend in different axial directions relative to other of said plurality of recesses, and wherein said different axial directions correspond to different angular orientations of illumination axes (B);
    collimators, the collimators being in respective recesses of the support structure, the collimators each being aligned with respective illumination axes (B);
    wherein each tongue is bent relative to other areas of the PCB to be oriented in a respective axial orientation (C);
    wherein each tongue is associated with a respective collimator such that the respective LED on the tongue is aligned with the collimator in the respective recess in the support structure and also with the respective illumination axis (B);
    wherein each tongue is held in its respective bent position against the support structure by a respective catch of the support structure which locks the tongue in place by clipping onto the tongue.

17. The medical lighting device according to claim 16:
    wherein the tongues of the PCB are flexible about respective bending axes (P); and
    wherein the axial orientations (C) of the tongues are perpendicular to the respective illumination axes (B).

18. The medical lighting device according to claim 16:
    wherein the lighting device is in a shape of a dome; and
    wherein the lighting device is connected to a movable suspension arm, the suspension arm being configured for suspension in an operating theatre.

19. The medical lighting device according to claim 16:
    wherein the tongues are each planar sections cut from the PCB, and are connected to the PCB at respective bending axes (P).

20. A method of assembling the medical lighting device according to claim 16, the method comprising:
    fastening the PCB to a rear side of the support structure;
    bending said plurality of tongues of the PCB towards the rear side of the support structure, until the LEDs of the tongues are positioned adjacent respective collimators; and
    locking the tongues against the support structure in a bent position by clipping the tongues under catches of the support structure.

* * * * *